United States Patent [19]

Brock-Fisher et al.

[11] Patent Number: 4,926,872
[45] Date of Patent: May 22, 1990

[54] ULTRASONIC TRANSDUCER SYSTEM AND METHOD FOR THE OPERATION THEREOF

[75] Inventors: George A. Brock-Fisher, Andover; Paul R. Kranz, Harvard; James R. Mniece, Waltham, all of Mass.; Karl E. Thiele, Derry, N.H.; Bernard J. Savord, Ithaca, N.Y.; Richard B. Smith, Tewksbury, Mass.

[73] Assignee: Hewlett-Packard Company, Palo Alto, Calif.

[21] Appl. No.: 173,763

[22] Filed: Mar. 28, 1988

[51] Int. Cl.$^5$ .............................................. A61B 8/00
[52] U.S. Cl. ................................... 128/661.01; 73/626
[58] Field of Search ..................... 128/660.05, 661.01, 128/661.09, 661.10; 73/626; 367/103, 105

[56] References Cited

U.S. PATENT DOCUMENTS

| | | | |
|---|---|---|---|
| 4,443,862 | 4/1984 | Buchner et al. | 73/626 X |
| 4,505,156 | 3/1985 | Questo | 73/626 |
| 4,528,854 | 7/1985 | Shimazaki | 73/626 |
| 4,542,746 | 9/1985 | Takamizawa | 73/626 X |
| 4,612,937 | 9/1986 | Miller | 73/861.25 X |
| 4,622,634 | 11/1986 | Fidel | 73/626 X |
| 4,628,738 | 12/1986 | Burchhardt et al. | 73/626 |
| 4,742,830 | 5/1988 | Tamano et al. | 73/861.25 X |

Primary Examiner—Francis Jaworski
Attorney, Agent, or Firm—Frank R. Perillo

[57] ABSTRACT

This invention provides an ultrasonic transducer system which utilizes a reconfigurable delay line to perform a variety of processing functions. In particular, for a preferred embodiment, the delay line utilized to sum the outputs of transducer elements is reconfigurable to provide serial processing of image scan lines while providing parallel processing of Doppler color flow scan lines. More particularly, the echo signals generated in response to the packet of color flow lines utilized to generate color flow information are applied in a predetermined way to two separate portions of the delay line, the portions of the delay line having different delay profiles, the resulting outputs being focussed to slightly different points in the image and thus providing color flow packets for two separate points in response to the transmission of a single packet of color flow lines. This results in a substantial enhancement of the system frame rate.

Other possible applications of the reconfigurable delay line in an ultrasonic scanning system are also discussed, and a packet serializer is disclosed which buffers, sequences, and preprocesses the received packet data.

23 Claims, 6 Drawing Sheets

ULTRASONIC TRANSDUCER SYSTEM AND METHOD FOR THE OPERATION THEREOF

FIELD OF THE INVENTION

This invention relates to ultrasonic transducer systems and more particularly to such systems utilizing a reconfigurable summing delay line to achieve selected processing of echo signals from ultrasonic transducer elements.

BACKGROUND OF THE INVENTION

Ultrasonic transducer systems are finding increasing applications in such fields as material testing, product testing and analysis, medical diagnosis, and other medical functions. Such systems, particularly when used for medical diagnosis, may provide image data which is displayed on a cathode ray tube or other suitable display to provide dynamic images of the heart, lungs, or other internal organs, and may also be operated in a Doppler or color-flow mode to indicate the direction and velocity of flow at a particular point of blood or other selected bodily fluid. With the latter type of data, the image appearing on the display may, for example, be in one color when the blood or other fluid is flowing in one direction, and in a contrasting color when the blood or fluid is flowing in the opposite direction. The intensity of the color indicates the rate of fluid flow in the indicated direction at the point. Many systems, particularly in the medical field, are adapted to simultaneously provide both image and color flow data. An example of such a system is the Hewlett Packard Ultrasonic Scanner Model No. 77020AC revision K.

In such systems, while a single scan line is adequate to obtain the data necessary for an image of the points being scanned on the line to be displayed, a packet of lines, for example from four to sixteen scan lines, may be required to provide the data necessary to produce a Doppler color flow image of blood or other fluid flow at the point. The large number of scan lines required to scan a target such as the heart to obtain color flow data indicative of blood flow at valves or other points therein, significantly reduces the frame rate at which such scans can be performed. This may cause an image distorting flicker of the resulting display. Reducing the number of scan lines reduces the ability of the system to determine and indicate flow rate and thus makes the data provided by the system less accurate and less useful. A need therefore exists for a relatively simple and inexpensive means of improving the frame rate of an ultrasonic transducer system of the type providing a Doppler color-flow display without reducing the number of scan lines in the packet scanning a given point to generate the color-flow data. Such means should also not interfere with the resolution of image data which may be generated concurrently with the color-flow data.

Another problem experienced with existing ultrasonic scanning systems is that, while such systems can be easily focused for a point at a particular depth, it is difficult to dynamically focus the system to remain in focus as the transmitted scan lines move deeper into the body, resulting in echo signals being received from successively deeper points. A particular problem in this regard is the delay line which may be utilized to sum the received echo signals from the transducer elements. The delay line is required because the echo wave front does not strike all of the transducer elements at the same time, resulting in the echo signals from the various transducer elements being out of synchronization. The received echo signals are applied to taps on the delay line in a manner such as to compensate for the variable times at which the signals are received, resulting in the summing of comparable points sensed by each of the transducer elements. However, as the echo signals come from deeper in the body, and thus further from the transducer elements, the differences in time at which the signals are received at the elements decreases. If the delays between taps on the delay line to which the received signals are applied remain constant, this results in the image being out of focus for the deeper points. However, if an attempt is made to switch the delay between taps in the middle of a scan line, the resulting transient may cause noise, and thus distortion of the image. Heretofore, there has been no acceptable solution to the problem of dynamically focusing the delay line. Thus, the delays are either selected for a particular depth with the image being slightly out of focus at other depths, or an average value is selected for the delays which results in the images being increasingly out of focus at near and far depths. A need therefore exists for a technique to permit the dynamic focussing of the summing delay line used in ultrasonic delay line systems without resulting in switching transient noise.

In addition to the specific problems identified above, other situations arise in ultrasonic transducer systems where, in response to selected input conditions, it may be desirable to alter the delays between taps or otherwise reconfigure the delay line, such as by converting it into two parallel lines rather than a single serial line. It would therefore be desirable if the delay line utilized in such systems could be designed so as to be reconfigurable in response to selected inputs or detected conditions, such reconfiguring occuring simply and inexpensively and with the addition of a minimum amount of circuitry.

SUMMARY OF THE INVENTION

In accordance with the above, this invention provides an ultrasonic transducer system which includes a plurality of ultrasonic transducer elements, a means for transmitting at least two different types of ultrasonic scan lines, for example, image lines and color flow lines, from the elements, a means for receiving ultrasonic echo signals from the elements in response to the different types of lines, a tapped delay line adapted to sum the received echo signals in a predetermined manner, and a means for utilizing an output of the delay line to display a representation of echo signals received in response to each type of transmitted line. In one embodiment, the invention is characterized by having a means for reconfiguring the delay line so as to cause serial processing of echo signals received in response to one type of line and to cause parallel processing of echo signals received in response to a second type of line. More particularly, the delay line may be configured as a single serial line when echo signals responsive to image lines are being summed, and may be configured as at least two parallel lines when echo signals responsive to color-flow lines are being summed. When the delay line is configured as two parallel lines, echo signals from selected elements may be applied to one of the lines and echo signals from the other elements applied to the other of the lines. However, it is preferred that echo signals received from at least selected ones of the elements in response to color flow lines be applied as inputs at selected points on both delay lines of the parallel pair. If the delay profiles in the two lines differ slightly, two separate echo signals may be obtained simultaneously from a single element and a single scan line, permitting a substantial improvement in the frame rate of the system for a given size of color-flow packet. A packet serializer may be provided to organize the information received from the delay lines, and provide such information to a color-flow processor as required. Switch means may be provided for reconfiguring the delay line, the switch means being operated in response to stored settings from a suitable storing means.

More generally, a tapped delay line means is provided in an ultrasonic transducer system which means is adapted to sum the received echo signals in a manner such as to compensate for differences in time at which echo signals are received at the elements. A means is provided for utilizing the output of the delay line means to display a representation of the received echo signals, and means are provided for controlling the configuration of the delay line means in response to selected system characteristics. For example, the delay line means may be controlled to cause serial processing or parallel processing of received echo signals. The delay line means may, for example, be configured so as to act as a means for dynamically focussing the system to the beam depth from which echos are being received. The configuring of the delay line may be accomplished through switch means which are set in response to selected system characteristics.

Invention also resides in the method of improving the frame rate in such ultrasonic transducer systems by utilizing the delay line to serially process image data and to parallel process color-flow data, the delay line being dynamically reconfigurable to accomplish this objective.

The foregoing and other objects, features and advantages of the invention will be apparent from the following more particular description of a preferred embodiment of the invention as illustrated in the accompanying drawings.

IN THE DRAWINGS

DETAILED DESCRIPTION

Figure 1A:
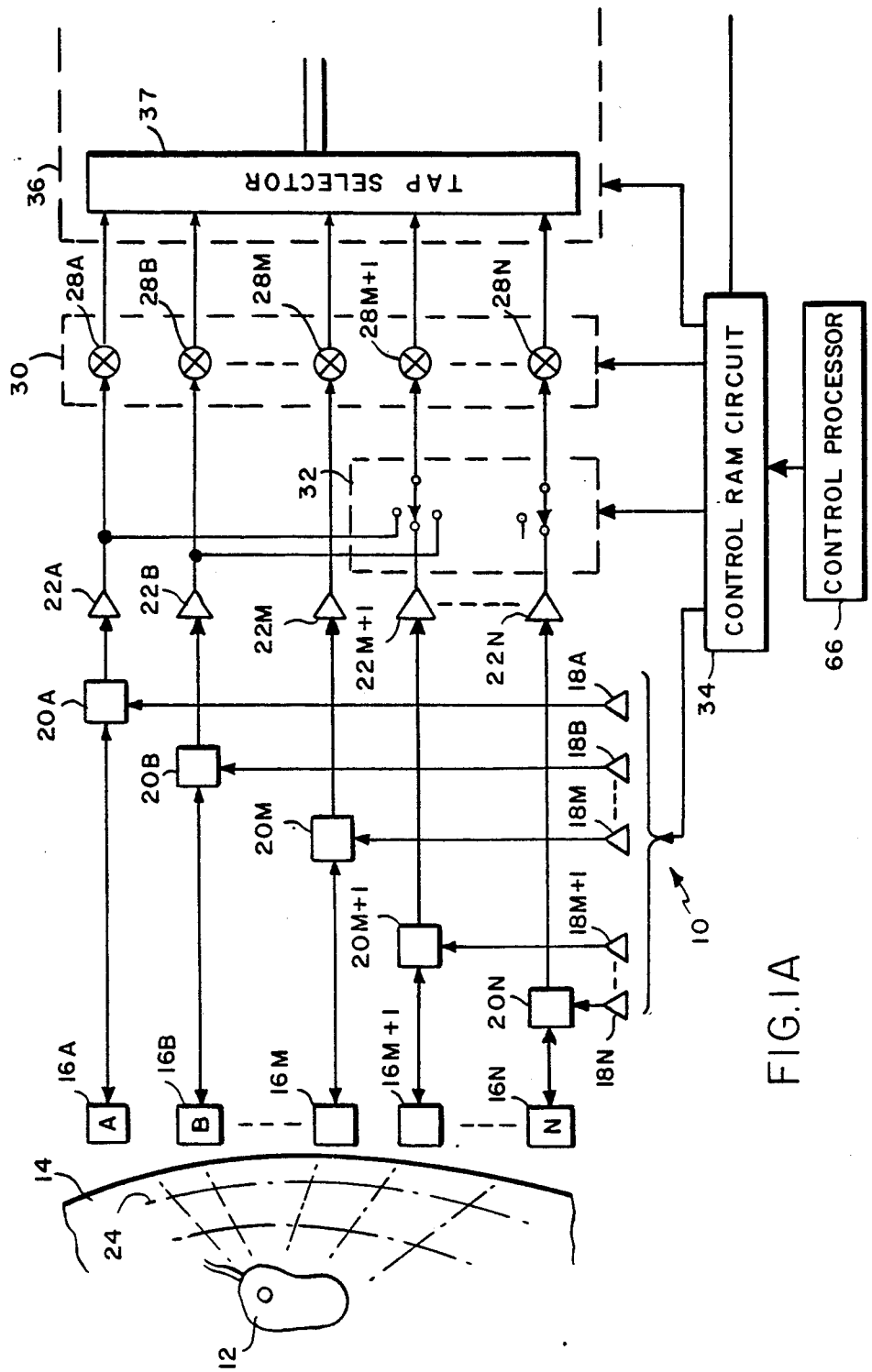
FIG. 1 is a schematic block diagram of an ultrasonic transducer system incorporating the teachings of this invention.
Figure 1B:
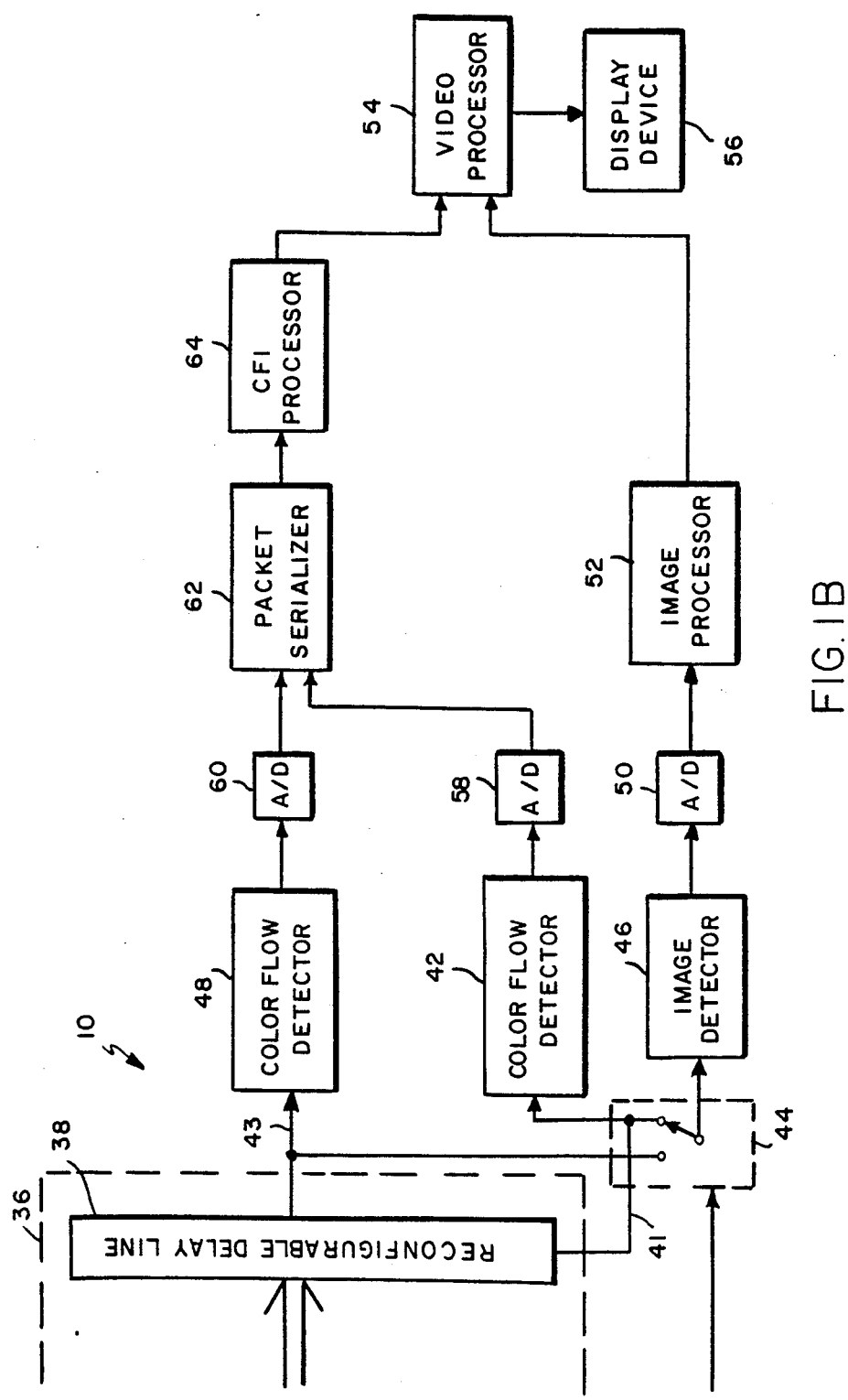

FIG. 1 shows the ultrasonic transducer system of this invention being utilized to scan the heart 12 of a person 14. It should, however, be understood that while, in the discussion to follow, the invention will be described with respect to a medical system, the invention is in no way to be construed as being limited to such applications.

The ultrasonic transducer system 10 includes a plurality of ultrasonic transducer elements 16A–16N. Each of the transducer elements may, for example, be a thin piece of piezoelectric crystal. In exemplary medical applications there may be 64 or 128 such elements.

Each transducer 16 is triggered by a signal from a corresponding transmitter 18A–18N which is applied to the transducer element through a suitable interface circuit 20A–20N which circuit protects the corresponding receiver 22A–22N for the element and performs an interface function. The timing and sequencing for the triggering of transducer elements 16 are selectively controlled to control, for example, the focusing of the scan line.

Echo signals from heart 12 which are produced in response to the transmitted ultrasonic signals form a front as illustrated by the lines 24 which fronts are at all points equally distant from the point from which the echo originates. Because of the difference in distance of the elements 16 from a point being scanned, and thus the difference in time at which a front 24 reaches various ones of the elements, the echo signals received at the transducer elements 16 from a given point are slightly out of phase. These signals are transmitted through interfaces 20 to receivers 22. For the embodiment of the invention shown in FIG. 1, the outputs from half of the receivers 22, receivers 22A through 22M (where $M=N/2$), are applied directly to the inputs of mixers 28A–28M in mixing circuit 30 and are also applied as one set of inputs to switching circuit 32. The outputs from the other half of the receivers, receivers 22M+1 through 22N, are applied as the second set of inputs to switching circuit 32. When switching circuit 32 is set as shown in FIG. 1, the echo signals from receivers 22M+1 through 22N are applied through the switching circuit to the corresponding mixers 28M+through 28N. However, when the switches 32 are transferred from the positions shown in FIG. 1 to their alternate position, the output from receiver 22A is applied in parallel to mixer 28A and to mixer 28M+1, the output from receiver 22B is applied in parallel to mixers 28B and 28M+2, and so on, with the output from receiver 22M being applied in parallel to both mixers 28M and 28N. When the switches 32 are in this alternate position, the outputs from receivers 22M+1–22N are not utilized.

The other input to each of the mixers 28A–28N is a signal of controlled phase from control RAM circuit 34 which functions in a manner known in the art to align the phases of the received echo signals, thus compensating in part for the slight variations which occur in the time, and thus the phase, at which the echo signals from a given point in the target are received at transducers 16. The outputs from the mixers 28 are applied to tap sequencer 37 in delay line circuit 36. The tap sequence determines, in a manner known in the art, the tap or taps on reconfigurable tapped delay line 38 which each mixer output is applied to. Delay line 38 is used to sum the echo signals received from the mixers in a manner such as to align the amplitude envelopes of these signals. For example, the tap sequencer may apply signals received from transducers at the same distance from the target point to the same delay line tap, the inputs to the taps being aligned in a manner such that inputs received from elements nearer the target point are delayed more than the inputs received from elements farther from the target point.

Figure 3:
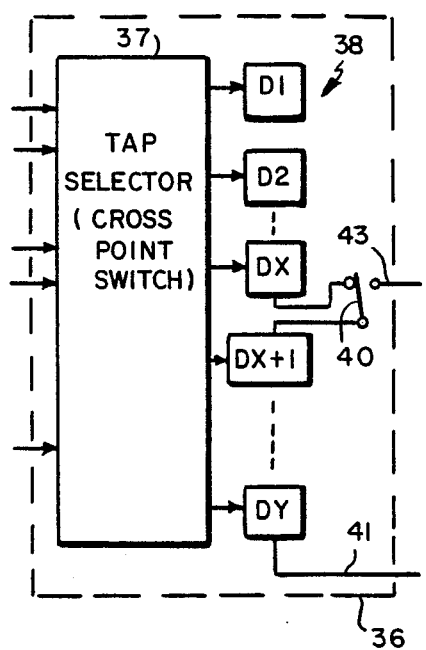
FIG. 3 is a more detailed schematic block diagram of a reconfigurable delay line circuit suitable for use with the embodiment of the invention shown in FIG. 1.

Referring to FIG. 3, tapped delay line 38 has a plurality of delay elements D1-DY. Since the outputs from a plurality of mixers may be applied to a single delay line tap, there need be no correlation between the number of transducer elements 16 and the number of delay line elements. At least selected ones of the delay line elements may be interconnected by switch means so that the delay line may be reconfigured to achieve selected processing objectives. More particularly, a switch 40 may be provided between delay line element DX and delay line element DX+1 (where X=Y/2), which permits the delay line 38 to be connected as a single serial line having Y elements as shown in FIG. 3, or to be connected as two parallel delay lines, each having X elements.

The output from delay line element DY on line 41 is connected as the input to color flow detector 42 and as one input to switch 44. The output from switch 44 is connected as the input to image detector 46. When switch 40 is transferred to the position not shown in FIG. 3, the output from delay line element DX on line 43 is connected as the input to color flow detector 48 and is the other input to switch 44. The detectors 42, 46 and 48 operate in a standard fashion to process the summed echo signals received from a given point by transducers 16 into analog voltage signals. The output from image detector 46 is applied through an analog-to-digital converter 50 to a digital image processor 52 which formats a received signal in standard fashion for application to video processor 54 which controls the display device 56. Display device 56 may, for example, be a cathode ray tube display. Similarly, the analog voltage outputs from color flow detectors 42 and 48 are applied through analog-to-digital converters 58 and 60, respectively, to the inputs of packet serializer 62. Packet serializer 62 performs two functions. First, as will be described in greater detail hereinafter, it interlaces the packets received from detector 42 and detector 48 so that color flow data from the appropriate detector is being applied to color flow image processor 64 at a given instant. Second, it serves as a buffer and preprocessor for processor 64, applying the corresponding word for a given point from a given color flow packet to processor 64 as the processor is ready to process this data. Processor 64 formats the received color flow data for application to the video processor which controls the display on display device 56.

Figure 5:
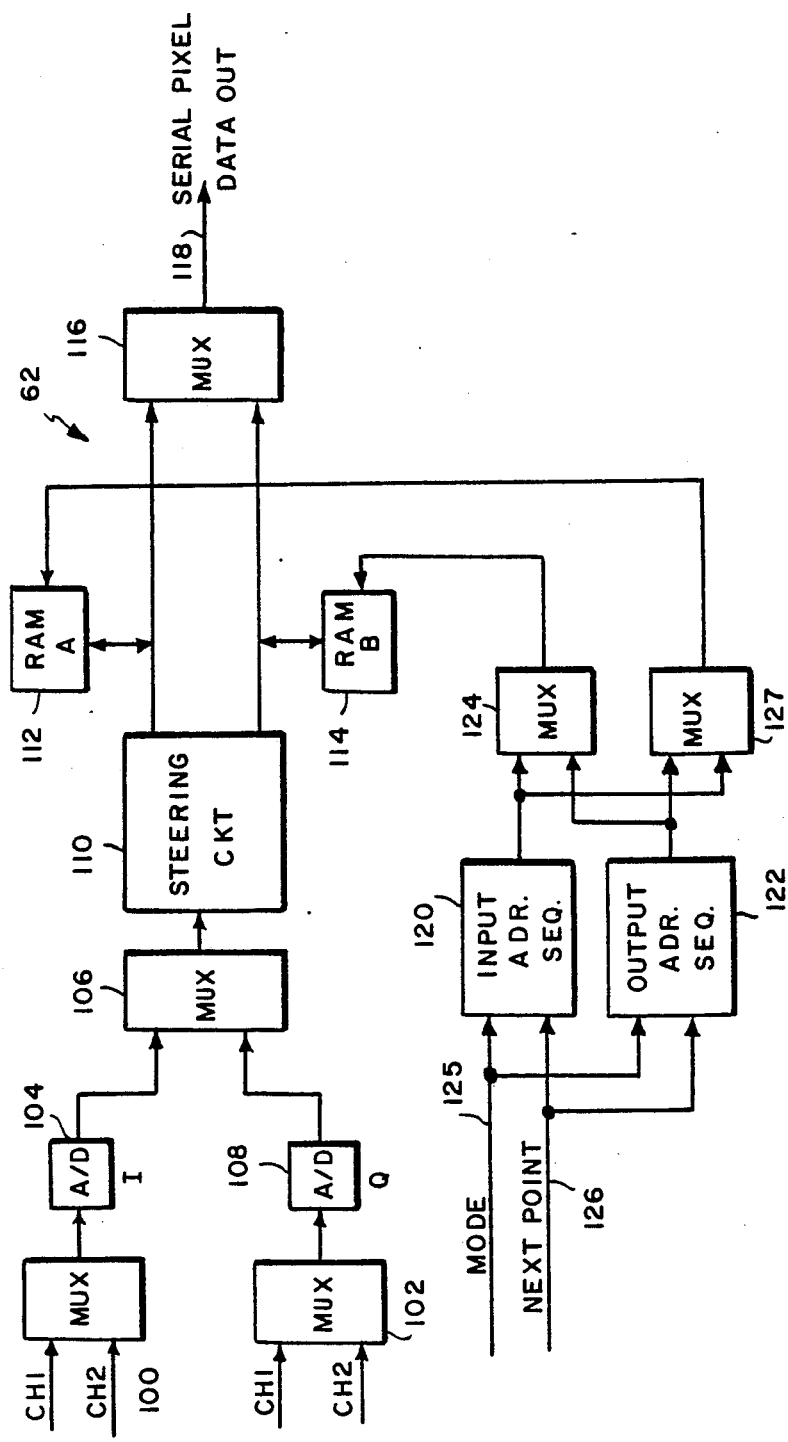
FIG. 5 is a schematic diagram of a packet serializer suitable for use with the embodiment of the invention shown in FIG. 1.

Referring to FIG. 5, a packet serializer suitable for use as the packet serializer 62 is shown. With the serializer of FIG. 5, A to D converters 58 and 60 are not required, and the outputs from detectors 42 and 48 are applied as inputs to multiplexers 100 and 102. The detectors divide the echo signals received from each point into an in-phase signal and a quadrature signal, with the in-phase signals from both detectors being applied for example to multiplexer 100 and the quadrature outputs from both detectors being applied to multiplexer 102. As is known in the art, the quadrature signals are required in order to unambiguously determine the direction of flow of the fluid being monitored, but not for determining its velocity. The signals at the output of the detector which are applied to multiplexers 100 and 102 appear simultaneously. The in-phase output from multiplexer 100 is applied through analog-to-digital converter 104 to one input of multiplexer 106, and the quadrature output from multiplexer 102 is applied through analog-to-digital converter 108 to the other input of multiplexer 106. Multiplexer 106 toggles between its inputs, applying for example first the in-phase output from multiplexer 100 from a given point, and then the quadrature output from multiplexer 102 from that point to steering circuit 110. Steering circuit 110 causes the inputs received from the detectors 42 and 48 to be applied to and stored in one of two random access memories (RAM A 112 or RAM B 114) until all of the data for a single color flow or parallel color flow packet from the detectors has been received and stored in the RAM, and then toggles to cause the next color flow or parallel color flow packet received from the detectors to be stored in the other one of the RAMs. The information concerning each input for each point is stored as a multibit word at a given memory address position. Circuit 110 is also operative to cause the RAM which is not having information read into it during a given cycle to have information read out from it, the outputs from each of the RAMs being applied through a multiplexer 116 to a pixel data output line 118 leading to CFI processor 64 (FIG. 1).

The address at which a given word, either an in-phase word or a quadrature word, is stored in the appropriate RAM 112 or 114, is controlled by an input address sequencer 120, and the word address from which data is read out from the appropriate RAM 112 or 114 is controlled by output address sequencer 122. One input to the address sequencers 120 and 122 is a mode signal or signals on line 125 from, for example, control processor 66 or control RAM circuit 34. The function of this signal will be described shortly. The other input to sequencers 120 and 122 is a next point clock signal on line 126. The output from multiplexer 124 is applied to control the addressing of RAM 114 for either input or output, and the output from multiplexer 127 is applied to control the addressing RAM 112 for either input or output.

As will be described in greater detail in conjunction with the operation of the packet serializer, the points appearing on a given color flow line are divided into blocks, each block having a predetermined equal number of points. For example, if there are 384 possible points on a color flow scan line at which readings may be taken, each line may be divided into three blocks of 128 points each. If there were four such scan lines in a packet, there would thus be twelve blocks of points in the packet. Similarly, if there were sixteen scan lines in a packet, there would be 48 blocks in a packet.

Figure 6:
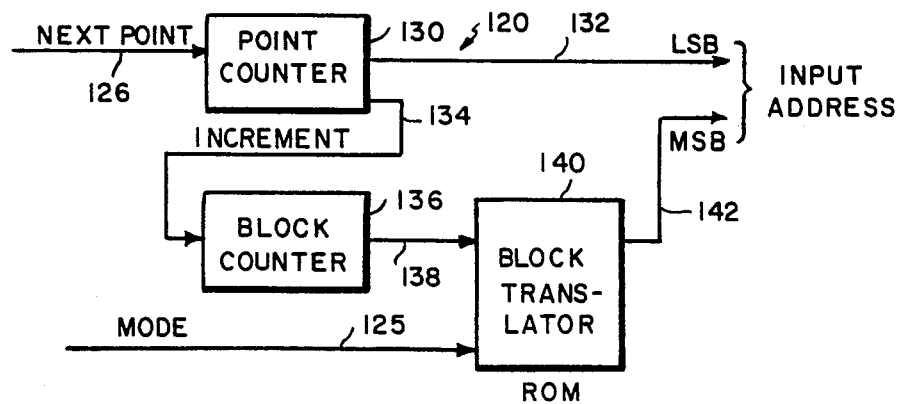
FIG. 6 is a schematic diagram of an input address sequencer suitable for use in the packet serializer of FIG. 5.

With the above in mind, FIG. 6 is a schematic block diagram of an input address sequencer suitable for use as the sequencer 120 in FIG. 5. The next point clock signal on line 126 is applied as the input to increment point counter 130. The output from point counter 130 on lines 132 contains the least significant bits of the input address applied through the multiplexer 124 or 127 to the appropriate random access memory.

When point counter 130 is full, it returns to 0 and generates an output on line 134 which is applied to increment block counter 136. The block count in block counter 136 is applied through lines 138 to block translater 140. The other input to block translater 140 is the mode information on lines 125. Block translater 140 may, for example, be a read-only memory (ROM) or other memory device which is utilized in a table lookup mode to produce on lines 142 the most significant bits of the address at which a given word, either an in-phase or quadrature word, for a given point are to be stored in the appropriate RAM. If the system were always operated with the same number of color flow scan lines and the same number of blocks for a given scan line, a block translater would probably not be required. The block translater, however, permits flexible operation of the system and efficient memory usage with varying numbers of color flow lines in the packet for a given point and varying numbers of blocks for a given scan line.

Figure 7:
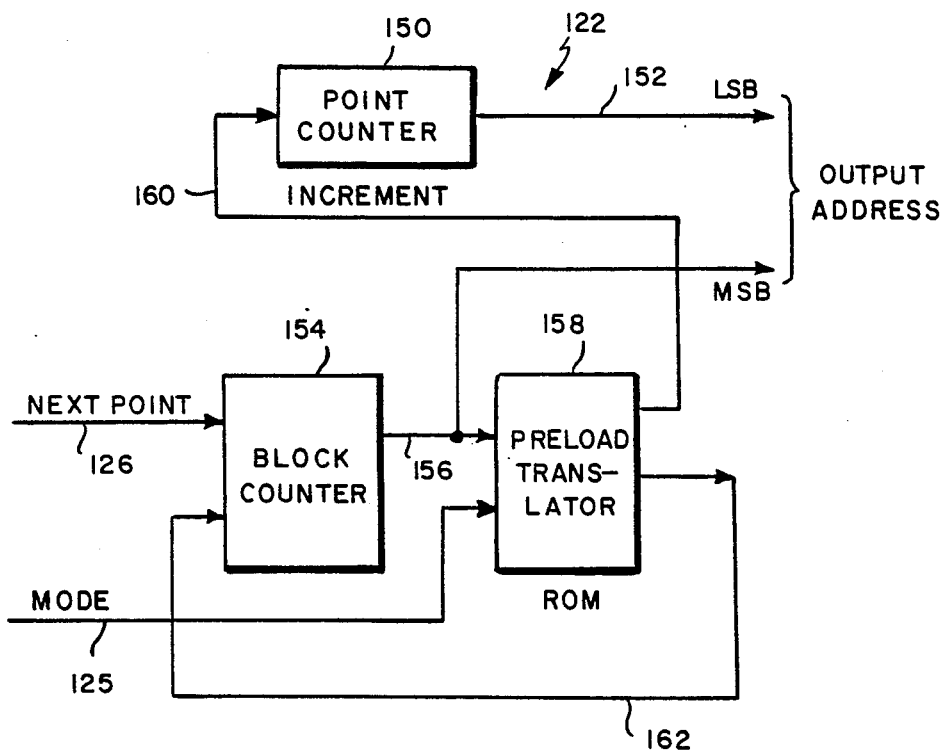
FIG. 7 is a schematic diagram of an output address sequencer suitable for use in the packet serializer of FIG. 5.

As was mentioned briefly above, and as will be discussed in greater detail hereinafter, while the information for a given color flow packet is read into RAM 112 or 114 a scan line at a time, the information is read out a pixel at a time (i.e., the information on each scan line for a given point being sequentially read out followed by the information for the next point on each of the scan lines). FIG. 7 shows an output address sequencer which may be used as the output address sequencer 122 in FIG. 5 to accomplish the read-out function. This circuit includes a point counter 150 which provides the least significant bits of the read-out word address on lines 152. In the output address sequencer the next point clock signal on line 126 is applied to increment block counter 154 in a manner to be discussed in greater detail hereinafter, the output on line 156 from block counter 154 being applied both as the most significant bits of the output address and as an input to preload translator 158. As for the input processor, translator 158 is a ROM or other memory operated in a table lookup mode which provides suitable block counter pre-load values taking into account the mode of operation of the system as indicated on line 125. The translator has an output on line 160 which increments point counter 150 and an output on line 162 which controls the pre-loading of block counter 154.

The operation of transmitters 18, the settings of switches 32, the phase control inputs to mixers 30, the tab selection for delay line circuit 36, the setting of switch or switches 40 in the delay line circuit, and the setting of switch 44, are all controlled from control RAM circuit 34 in response to inputs received from control processor 66. The exact manner in which circuit 34 and processor 66 function to control the operation of the system shown in FIG. 1 will vary with application. However, one way in which this may be accomplished is for circuit 34 to include a random access memory which stores the desired control outputs for each operating condition of the circuit. Thus, when an input is received from control processor 66 indicating a particular operating condition of the system, this input is used to address the control RAM in table lookup fashion, causing the proper control outputs to be generated by circuit 34. Since some of the control outputs may not be utilized at the same time, suitable timing or buffering circuitry may be required to assure that each control signal is applied to the system when required. For large systems, involving for example 64 or 128 transducer elements, the number of control outputs required may be sufficiently large so that the control data may be stored in two memories for parallel readout, or other circuitry may be provided to permit the control functions to be performed at the rate required.

Figures 2, 2A:
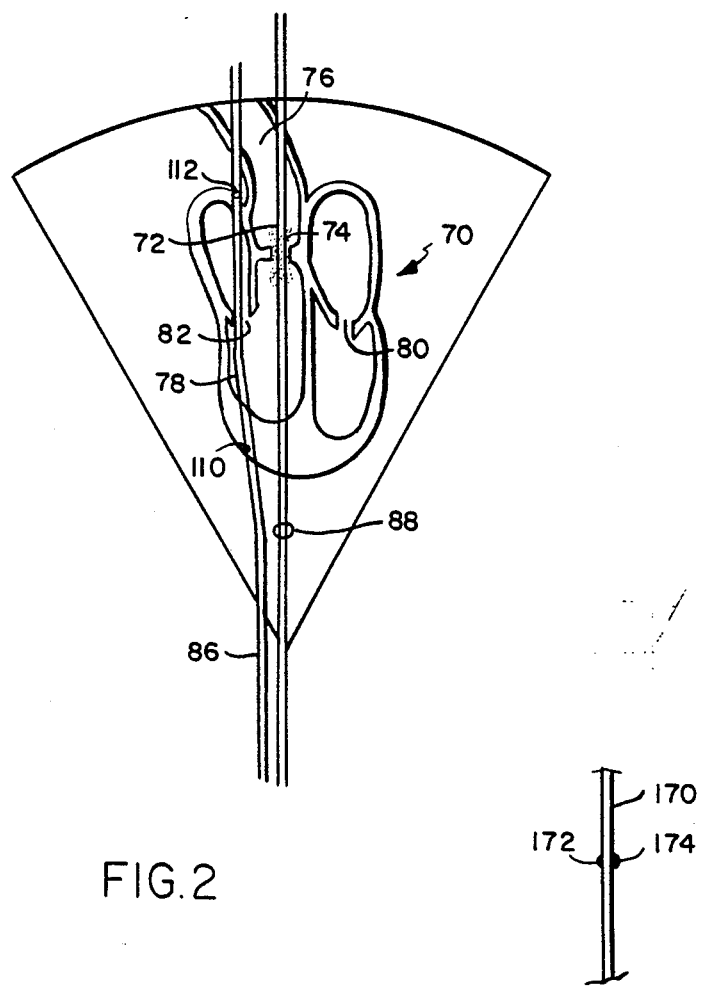
FIG. 2 illustrates an image of the type obtainable with a system of the type shown in FIG. 1.
FIG. 2A illustrates how two points are obtained during a single scan when in a parallel mode.

FIG. 2 is a diagram showing an illustrative display which might be obtained utilizing the system of FIG. 1. This display includes both an image 70 of the heart 12 being scanned, and color flow data illustrated by, for example, the shaded area 72, showing the direction and velocity of blood flow through the aortic valve 74 from the aorta 76 to the right ventricle 78. Blood flow through other valves such as the mitral valve 80 between the left atrium and the left ventricle and the tricuspid valve 82 between the right atrium and the right ventricle may also be shown.

The image 70 and color flow 72 are generated by the transducers 16 generating a plurality of scan lines which scan across the field of view shown in FIG. 2 from, for example, left to right, one such line 86 being shown in FIG. 2. In areas where the scan lines are passing through points where color flow data is also desired, a packet of color flow lines, such as the scan lines 88 passing through aortic valve 74, is generated at such point interspersed with the scan lines. Thus, for example, if 16 color flow lines were being generated as a packet to indicate the direction and velocity of blood flow through aortic valve 74, these lines might be generated in two bursts of eight color flow lines each with an image scan line between each packet burst.

Referring again to FIG. 1, when image lines are being generated, the system would be configured as shown in FIG. 1 with the output of each transducer element 16, which output is an echo signal received in response to the corresponding scan line, being applied through the corresponding receiver 22 and mixer 28 to the appropriate tap on a single series connected delay line 38. The output from the delay line is applied through switch 44 and image detector 46 to image processor 52, causing image information for the line 86 being scanned to be displayed on display 56. This sequence of operation is conventional, and the manner in which this operation is performed is not specifically part of the present invention. An example of an ultrasonic transducer system which operates in this manner is the beforementioned Hewlett Packard Ultrasonic Scanner Model No. 77020AC revision K.

When a point in the image is reached where color flow data is desired, the resulting input to control RAM circuit 34 causes inputs to be applied to switches 32 and to delay line circuit 36 to transfer switches 32 and 40 to their alternate positions (i.e. to the positions not shown in FIGS. 1 and 3). Thus, if 128 transducer elements 16 are utilized when the circuit is operating in its image mode, only 64 of those transducers, transducers 16A–16M are utilized when the system is in its color flow mode, the outputs from the other 64 transducers, transducers 16M+1–16N, being unused. The outputs of receivers 22A–22M are applied through appropriate mixers 28 and tap selector 37 to appropriate taps on the parallel pair of delay lines formed when switch 40 is transferred. Thus, the output from each receiver 22A–22M is applied to an appropriate tap on a delay line formed of elements D1–DX (FIG. 3), and to an appropriate tap on a delay line formed by elements DX+1–DY. As previously noted, two or more inputs from the receivers may be applied to each input on each of the two delay lines. However, the delay profiles of the two delay lines differ slightly. For example, even though the output from a given receiver is applied to both delay lines, the output may be applied to a different point on one of the lines from the other line. The phase inputs to the corresponding mixers to which the outputs from a given receiver are applied may also differ slightly. This means that the output from one of the delay lines is focused on a slightly different point than the output from the other delay line, resulting in there being two separate echo signal outputs from two slightly spaced points in the scan area in response to a single transmitted color flow scan line. The width of the transmitted color flow line is great enough to permit this splitting to occur while still remaining within its scan area. For example, referring to FIG. 2A, a scan line 170 is shown which is wide enough to include within its scan path two spaced points 172 and 174, the output from one of the delay lines, for example the delay line having elements D1-DX, may be focused to the point 172 while the other delay line, for example the delay line having element DX+1-DY, is focused to the point 174 slightly displaced from the point 172 but still within the scan line 170.

Thus, color flow line packets from two separate points may be obtained in response to a single packet of transmitted color flow lines. Therefore, with the previous example where a color flow packet was formed of 16 color flow lines which occured in two bursts of eight lines each, and utilizing the teachings of this invention, color flow data for two points can be obtained with the same 16 line packet rather than requiring two packets as in the prior art. This technique thus permits a substantial reduction in the number of color flow lines which must be transmitted in order to obtain a given resolution of color flow data, and thus permits a substantial improvement in the frame rate of the system, eliminating flicker which might occur as a result of the frame rate being too low.

The outputs from each of the parallel connected delay lines are applied through a corresponding color flow detector (42 or 48) and analog-to-digital converter (58 or 60) to the input of packet serializer 62. As previously indicated, the packet serializer stores the indications of the color flow echo signals for the lines of a packet received from detectors 42 and 48 as this information is received in a RAM and then when a full parallel packet has been received, utilizes the stored information to control the display while loading the next parallel packet into a second RAM.

Figure 8:
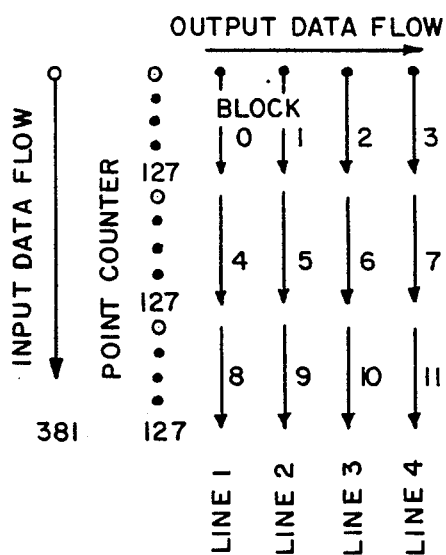
FIG. 8 is a diagram illustrating the storage and readout of data in a RAM of the packet serializer of FIG. 5.

More particularly, the in-phase and quadrature inputs from, for example, detector 42, are applied through multiplexers 100 and 102 (FIG. 5) and A/D converters 104 and 108 to multiplexer 106. Multiplexer 106 selects one of these signals, for example, the in-phase signal from multiplexer 100 and passes it through steering circuit 110 to be stored in one of the RAM's for example, RAM A 112. The address in RAM 112 at which the digital word indicative of the in-phase value at the first point on the first scan line of the packet is stored is determined by input address sequencer 120. Referring to FIG. 8, it will be assumed that this address is the address for block 0 point 0. It will be further assumed that there are three blocks of 128 in phase/quadrature point pairs 128 points each on each scan line, and that there are four scan lines in each packet. The blocks are numbered as shown in FIG. 8 with blocks 0, 1, 2 and 3 being the first blocks respectively for each of the four scan lines. Thus, the three blocks for the first scan line of the packet are numbered 0, 4 and 8. After the in-phase word for the first point has been stored at address block 0 point 0, multiplexer 106 passes the quadrature word for the first point of the first line to RAM 112 which word is stored at address block 0, point 1. Succeeding in-phase and quadrature inputs for the first scan line are stored in successive point addresses in block 0 until 128 such point pairs have been stored. The 129th pair is then stored at address point 0 of block 4. This process is then repeated with 128 point pair positions in block 4 being filled. The 256th point input to RAM 112 from scan line 1 is then stored in the point 0, block 8 address position of RAM 112, and the remaining inputs of the first scan line are stored in the remaining point positions of block 8. This process is then similarly repeated for the remaining three color flow lines of the packet until the entire color flow packet has been stored in RAM A. Simultaneously, data from detector 48 is stored in the upper address space of RAM 112 by setting the most significant bit (MSB) to 1. The block and point addressing are the same.

The loading of RAM B 114 is performed in the same manner previously described for the loading of RAM A. RAM A 112 is, however, read out in a different sequence from the sequence in which information was stored therein. More particularly, referring again to FIG. 8, the information stored at point 0 for blocks 0, 1, 2 and 3 all correspond to the same point in the target. Color flow image processor 64 (FIG. 1) therefore needs the color flow information for this point from all four of the color flow lines in order to make the color flow determination for this point. In order to facilitate the operation of the color flow image processor, the packet serializer therefore reads out the information at points 0 and 1 in blocks 0, 1, 2 and 3 in sequence to the processor. The readout then returns to block 0 to read out points 2 and 3 in this block followed by points 2 and 3 in block 1, points 2 and 3 in block 2, and points 2 and 3 in block 3. The next point read out is points 4 and 5 in block 0, followed by points 4 and 5 in blocks 1, 2 and 3, in that order. This process is repeated until all of the points in the first block for each of the scan lines has been read out. The readout then starts with points 0 and 1 in block 4 and proceeds to read out point 0 in block 5, points 0 and 1 in block 6 and points 0 and 1 in block 7. The readout then returns to block 4 to read out points 2 and 3 in this block, with the corresponding points being read out in sequence in blocks 4, 5, 6, and 7, until all points in the second block of each line of the packet have been read out. The process is then repeated for the third block for each line of the packet. When point 127 of block 11 has been read out, the readout of RAM A has been completed, with respect to the first packet, and this RAM is ready to read out the parallel packet stored in its upper address space. The read out sequence is identical.

The toggling between storing information in one of the RAMs 112 or 114 while reading out information from the other RAM to control the CFI processor is repeated until all color flow packets in a frame have been processed. The packet serializer thus serves as a relatively simple and inexpensive buffer and preprocessor for the color flow image processor, transforming the color flow data which is received a scan line at a time from the image detector into the pixel data required by the CFI processor.

While in FIG. 8 the packet contained only four lines, the packet serializer is adapted to operate with packets of any desired size. For example, if an eight-line packet were utilized, the first blocks for the eight scan lines would be numbered 0-7 respectively, the second blocks of each scan line would be numbered 8-15, respectively, and the third blocks of each scan line would be numbered 16-23, respectively. Block translator 140 in input address sequencer 120 would make the necessary adjustments to assure that the inputs for a given scan line were stored in the appropriate address positions in the RAM, and preload translator 158 in output address sequencer 122 would assure that the point counter 150 and block counter 154 were properly set at each point during a readout operation, so that the appropriate word was being read out to the processor at each instant. The sequence in which the words are read into and read out of memory would otherwise be the same as that previously described for the four-line packet, except that during the readout operation, the word for the corresponding point on eight lines of the packet would be read out in sequence rather than the corresponding word for four lines.

While in FIG. 8, information has been shown as being read in vertically and read out horizontally, it is apparent that this sequence could be reversed. Similarly, the manner in which the packets are numbered could be reversed so that the blocks for a given color flow line could be sequentially numbered. With either of these changes, the translators would be configured to cause the word for a given point on a given scan line to be read in and read out at the appropriate time and at the appropriate address position. Similarly, as shown in the figures, the reading in and reading out occur with the system set for the same mode. This is not a limitation of the system, and the system could be configured either to provide separate mode inputs, which inputs may be the same or different, to the input and output sequencers, or it may provide a mode input only to the input sequencer, which mode input is stored with the input and to obtain the mode for the output sequencer by reading the mode information stored with the packet information being read out. The packet serializer could also be used with prior art systems where there is only a single output from the delay line. In such applications, the packet serializer would still perform the buffering and preprocessing functions and could still toggle between two memories so that one memory is being read out while the other one is being loaded.

Control processor 66 continuously applies inputs to circuit 34 indicating whether the line currently being scanned is an image line or a color flow line and, in response to such inputs, circuit 34 assures that all of the switches and other controls for the circuit are appropriately set for the line being scanned.

It is noted that, while the system produces the same number of packet lines for color flow images as prior art systems, the lines are obtained using only half as many transducer elements. Since a larger number of elements gives better focusing, and therefore better resolution, permitting smaller body parts to be more easily seen in the image, it is desirable that the maximum number of elements be utilized for image data. However, precise focusing and high resolution are not as essential for color flow data which does not rely on detailed images. Therefore, resolution can be sacrificed for color flow images to improve frame rate without a degradation in the performance of the system. Thus, by switching the system to provide serial processing for image data and parallel processing for color flow data, high resolution is obtained where required for the image data, which data requires a substantially smaller number of scan lines per point, while a substantially improved frame rate is obtained by sacrificing resolution where it is not required for color flow data while obtaining substantial frame rate improvement because of the large number of lines required for color flow data. An optimum tradeoff between frame rate and resolution is thus achieved.

Figure 4:
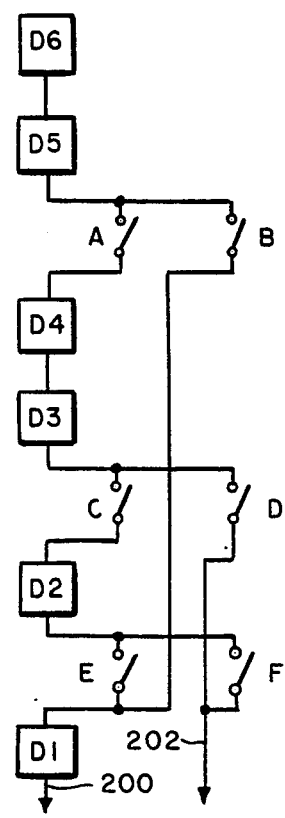
FIG. 4 is a schematic diagram of an exemplary delay line suitable for use in practicing the teaching of this invention.

While in the discussion so far the reconfigurable delay line circuit 36 has been utilized to improve the frame rate where color flow data is being generated in an ultrasonic transducer system, a reconfigurable delay line circuit may also be utilized to perform other processing functions in such an ultrasonic system. FIG. 4 illustrates a delay line 38 having switches 44 between at least selected ones of the delay line elements. For purposes of illustration, only six elements are shown in FIG. 4, although a delay line utilized in an ultrasonic scanning system of the type contemplated by this invention would normally have a much larger number of elements, for example, 90 to 100 elements. For purposes of illustration, it will be assumed that delay elements D1 and D2 have a shorter delay, for example, 100 nano seconds (ns) while delay elements D3-D6 have longer delays, for example, 200 ns each. With the configuration of switches shown in FIG. 4, if switches A, C and E are closed, the delay line elements are connected in series resulting in a single output on line 200 from delay line element D1. If switches B, C and F are closed and the remaining switches are open, the delay line is configured as two parallel lines each having a 500 ns delay. The first line consists of elements D1, D5 and D6, and has an output on line 200. The second line consists of elements D2, D3 and D4, and has an output on line 202. The switches 40 also permit the delay line 38 to be configured in a variety of other ways, either as a single serial line, as parallel lines or otherwise. It is apparent that with a larger delay line, having switches either between each pair of delay line elements or between selected delay line elements, an almost infinite variety of delay line configurations is possible.

FIG. 1 illustrates one additional way in which the reconfigurable delay line 38 may be utilized to enhance performance in an ultrasonic scanning system. As previously discussed, one problem in an ultrasonic scanning system is that the focus for a point such as point 110 on scan line 86 (FIG. 2) which is at a particular depth, is different than the focus for point 112 at a different depth on this line. In particular, the delay required between taps on delay line 38 is less for point 112 on scan line 86 than it is for point 110. The reason for this is that, as the scan lines get deeper into the body and thus farther from the ultrasonic elements 16, the delay required to maintain the echo signals received at each of the transducers in synchronization decreases. However, if an effort is made to switch the delay elements during a scan line, the resulting transients will cause noise in the output which will result in a distortion of the displayed image.

In FIGS. 1 and 3, this problem is overcome by transferring switches 32 and 40 so that the output from each receiver 22 is applied as an input to two parallel-connected delay lines. The delay line 38 and the inputs thereto are thus configured in the same way previously described for color flow lines. However, the output from only one of the two parallel-connected delay lines is utilized at any given time. Thus, when switch 44 is set as shown in FIG. 1, the output from the lower portion of the delay line 38 is applied through image detector 46 to control the image displayed on display device 56, while when switch 44 is transferred to the alternate position, the output from the upper half of the delay line is utilized to control the displayed image. This permits the delay line being utilized to have the delay necessary to provide proper focusing at the point along line 86 from which echos are being received at a given instant, while the portion of the line not being utilized is switched to provide delays between taps in that portion of the delay line to provide proper focusing at points along line 86 at greater depth. Switch 44 may then be transferred to accept outputs from the reconfigured delay line portion having the proper delays between taps for the greater depth at the point where echo signals from these depths are being received. This process may be repeated as often as required, with the unused portion of the delay line having its delays altered while the other portion of the delay line is being used to focus the echo signals. Thus, by utilizing a reconfigurable delay line, optimum focusing is achieved a each point along the scan line without introducing undesired transients into the output resulting from the delay line switching. It is noted that this procedure does result in some degradation in the resolution of the system since fewer elements are available to provide echo signal outputs. However, in some applications, the loss in resolution is more than offset by the improved focusing.

While for the embodiment shown in FIG. 1, only half of the transducer elements 16 are utilized when the system is configured to provide parallel delay lines, this is not a limitation on the system, and other combinations of inputs to the parallel delay lines are possible while still remaining within the teachings of the invention. For example, the outputs from receivers 22A-22M could be applied as inputs to the delay line formed from elements D1-DX while the outputs from receivers 22M+1-22N could be applied as inputs to the delay line formed from delay elements DX+1-DY. With slightly different delay profiles in the two lines, this would still provide two color flow echo lines in response to a single color flow scan line. Further, while for the preferred embodiment, the delay line has been split into two segments to enhance frame rate for color flow lines, in some applications it may be desirable to split the delay line into three or more parallel delay lines to further enhance frame rate. The process for doing this would be substantially the same as that described above with two parallel connected delay lines, except that, for example, each output from the upper third of the receivers 22 would be applied as an input to each of the three delay lines, and there would be three color flow detectors and three analog-to-digital converters applying inputs to packet serializer 62.

In addition, for the preferred embodiment parallel processing to improve frame rate could also be employed for image lines or other scan lines. For example, since an infant's heart beats faster than an adult's, a higher frame rate for the system may be desirable when doing pediatric imaging. However, as previously indicated, this increase in frame rate is achieved at the cost of some loss in resolution. Further, while three applications for the reconfigurable delay line have been discussed above, it is apparent that the reconfigurable delay line could be utilized to sum the receiver outputs in a variety of different ways to achieve a variety of processing functions in an ultrasonic scanning system.

Also, while the reconfiguration discussed above is between series and parallel mode, it is also possible, if required for a particular application, to configure the line in a series-parallel mode, to vary the delays between all or selected ones of the taps to compensate for variations in ultrasonic frequency or for other processing purposes or to reconfigure the line in some other way.

Further, while in the discussion so far, it has been assumed that delay line 38 is in hardware form, it is apparent that the invention could be practiced utilizing any element, either hardware or software, which is suitable for performing the delay and summing function of the delay circuit 36. Thus, the terms "delay line", "delay line circuit" and "delay line means" are intended to include any such device, and are not strictly limited to a standard hardware tapped delay line. Further, while the various switches shown in the drawings are shown for purposes of illustration as electrically controlled mechanical switches, it is apparent that these functions would normally be performed by various types of electronic switches. As previously indicated, applications for the invention outside the medical field are also possible.

Thus, while the invention has been particularly shown and described above with reference to a preferred embodiment, the foregoing and other changes in form and detail may be made therein by one skilled in the art without departing from the spirit and scope of the invention.

What is claimed is:

1. An ultrasonic transducer system comprising:
a plurality of ultrasonic transducer elements;
means for transmitting at least two different types of ultrasonic lines from said elements to a selected target;
means for receiving ultrasonic echo signals from said elements in response to said at least two different types of lines;
a tapped delay line adapted to sum the received echo signals in a predetermined manner;
means for utilizing an output of the delay line to display a representation of echo signals received in response to each type of transmitted line; and
means for configuring the delay line so as to cause serial processing of echo signals received in response to one type of line and to cause parallel processing of echo signals received in response to a second type of line.

2. A system as claimed in claim 1 wherein the one type of said lines are image lines and wherein the second type of lines are color flow lines.

3. A system as claimed in claim 2 wherein said configuring means includes means for configuring said delay line as a single serial line when echo signals responsive to image lines are being summed, and means for configuring said delay line as at least two parallel lines when echo signals responsive to color flow lines are being summed.

4. A system as claimed in claim 3 wherein the echo signals received from selected elements in response to color flow lines are applied to one of the parallel delay lines and echo signals received from other of said elements in response to color flow lines are applied to another of the delay lines.

5. A system as claimed in claim 3 wherein echo signals received from at least selected ones of the elements in response to color flow lines are applied as inputs at selected points on both delay lines of the parallel pair.

6. A system as claimed in claim 5 wherein the delay profile provided by one of said delay lines is different than the delay profile provided by another of said delay lines, whereby at least two parallel summed echo signals are obtained in response to a single transmitted color flow line.

7. A system as claimed in claim 6 wherein the means for utilizing includes a packet serializer, means operative when the delay line is configured for parallel processing for applying the outputs from both delay lines of a parallel pair to said packet serializer, and a color flow processor, said packet serializer storing the summed echo signals corresponding to selected color flow lines and applying portions of such stored signals to said processor in a predetermined sequence.

8. A system as claimed in claim 7 wherein a predetermined number of color flow lines are utilized to scan a given point at which color flow information is required; and wherein said packet serializer applies data for the corresponding pixels for the echo signals from one of said delay lines for the color flow lines scanning a given point to said processor until all pixels for said echo signals have been processed, and then applies data for corresponding pixels for the echo signals from the other of said delay lines for the same color flow lines formed to scan a different point to the processor.

9. A system as claimed in claim 5 wherein the means for utilizing includes a packet serializer, means operative when the delay line is configured for parallel processing for applying the outputs from both delay lines of a parallel pair to said packet serializer, and a color flow processor, said packet serializer storing the summed echo signals corresponding to selected color flow lines and applying portions of such stored signals to said processor in a predetermined sequence.

10. A system as claimed in claim 1 wherein said means for configuring includes switch means adapted to configure said delay line in at least two different configurations, means for storing settings of said switch means for selected types of lines, and means responsive to the system transmitting a given type of line for utilizing the stored settings to control said switch means to properly configure said delay line.

11. An ultrasonic transducer system comprising:
a plurality of ultrasonic transducer elements;
means for transmitting ultrasonic signals from said elements to a selected target;
means for receiving ultrasonic echo signal from said elements, the echo signals received by at least some of the elements from a given target arriving at a time different from the time at which such echo signals arrive at other of said elements;
tapped delay line means adapted to sum the received echo signals in a predetermined manner;
means for utilizing an output of the delay line means to display a representation of the received echo signals; and
means for controlling the configuration of said delay line means in response to selected system characteristics.

12. A system as claimed in claim 11 wherein said means for controlling is adapted to control said delay line means to cause serial processing or parallel processing of received echo signals.

13. A system as claimed in claim 12 wherein said means for transmitting is adapted to transmit at least two different types of ultrasonic signals; and wherein said means for controlling is adapted to cause serial processing of first echo signals received in response to one type of transmitted signals and parallel processing of second echo signals received in response to a second type of transmitted signal.

14. A system as claimed in claim 13 wherein said means for controlling includes means for configuring said delay line means as a single serial line when first echo signals are being summed, and means for configuring said delay line means as at least two parallel lines when second echo signals are being summed.

15. A system as claimed in claim 14 wherein the echo signal from at least selected ones of said elements may be applied as inputs at selected points on one or more of said parallel connected delay lines; and including means for controlling the delay lines and the points on the delay lines to which each echo signal is applied.

16. A system as claimed in claim 15 wherein said means for controlling includes switch means, and means responsive to the echo signal being summed for selectively setting said switch means.

17. A system as claimed in claim 11 wherein said means for controlling includes switch means, and means responsive to said selected system characteristics for setting said switch means to selectively configure said delay line means.

18. A system as claimed in claim 17 wherein said means for controlling includes means for storing settings of said switch means for selected system characteristics, and means responsive to said selected system characteristics for utilizing the stored settings to control said switch means to properly configure said switch means.

19. A system as claimed in claim 11 wherein said means for transmitting may transmit scan lines which penetrate to successively greater depths in the target; and including means for dynamically focusing the system to the target depth from which echos are being received.

20. A system as claimed in claim 19 wherein said means for dynamically focusing includes said means for controlling, said means for controlling including means for configuring said delay line means as at least two parallel delay lines, means for applying an echo signal received from an element to both delay lines, said means for selectively utilizing the outputs from at least one of said delay lines, and means operative during a period when the output from one of said parallel delay lines is not being utilized for reconfiguring said delay line to alter the delay thereof between at least selected active taps.

21. In an ultrasonic transducer system of the type wherein both image data and Doppler color flow data are simultaneously displayed, a plurality of color flow scan lines from ultrasonic transducer elements being required for each color flow data point, a method of improving the frame rate of the system for a given number of scan lines comprising the steps of:
utilizing a tapped delay line means as a single serial line to serially sum image data from the transducer elements;
switching the delay line means to function as at least two parallel lines to parallel process color flow data from the transducer elements;
serializing the outputs from the parallel delay lines;

utilizing the serially summed image data to control the display of image data; and utilizing the results from the serializing step to control the display of color flow data.

22. A method as claimed in claim 21 wherein the parallel processing of color flow data includes the steps of providing a different delay profile for each of the parallel delay lines to focus the delay lines to slightly different points within each transmitted color flow line.

23. An ultrasonic medical imaging system of the type providing both an image of a body part and a Doppler color flow indication of the direction and velocity of flow of a body fluid at least selected points in the body part, comprising:

a plurality of ultrasonic transducer elements;

means for selectively causing said elements to transmit either ultrasonic image scan lines or ultrasonic color flow scan lines, a packet of said color flow scan lines being required to obtain color flow data for a given point;

means for receiving first ultrasonic echo signals from the elements in response to said image scan lines and second ultrasonic echo signals from the elements in response to said color flow scan line;

a reconfigurable tapped delay line;

means for configuring said delay line as a single serial line when said first echo signals are being received;

means for configuring said delay line as at least two parallel delay lines when said second echo signals are being received, each of said parallel delay lines having a different delay profile so that said delay lines are focused to slightly different points from which color flow data is to be obtained;

means for applying said first echo signals to selected taps on the single serial line and for applying the second echo signals to selected taps of the parallel lines;

means responsive to the output of the delay line when first echo signals are applied thereto for displaying an image of the body part; and means responsive to the outputs from the parallel delay lines when second echo signals are applied thereto for displaying an indication of the body fluid flow direction and velocity at the different points to which the delay lines are focused, whereby the frame rate of the system is enhanced by permitting color flow indications to be obtained at two or more points from a single packet of color flow scan lines.

* * * * *